US010434044B2

(12) United States Patent
Latta et al.

(10) Patent No.: US 10,434,044 B2
(45) Date of Patent: *Oct. 8, 2019

(54) BUFFERED MICROENCAPSULATED COMPOSITIONS AND METHODS

(71) Applicants: Mark A. Latta, Omaha, NE (US); Stephen M. Gross, Omaha, NE (US); William A. McHale, Collegeville, PA (US)

(72) Inventors: Mark A. Latta, Omaha, NE (US); Stephen M. Gross, Omaha, NE (US); William A. McHale, Collegeville, PA (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,554

(22) Filed: Oct. 24, 2017

(65) Prior Publication Data

US 2018/0042826 A1 Feb. 15, 2018

Related U.S. Application Data

(60) Division of application No. 13/619,128, filed on Sep. 14, 2012, now Pat. No. 9,814,657, which is a continuation-in-part of application No. 12/768,696, filed on Apr. 27, 2010, now Pat. No. 8,889,161.

(60) Provisional application No. 61/172,939, filed on Apr. 27, 2009.

(51) Int. Cl.
| | |
|---|---|
| *A61K 8/11* | (2006.01) |
| *A61K 33/06* | (2006.01) |
| *A61K 33/16* | (2006.01) |
| *A61K 47/02* | (2006.01) |
| *A61K 6/00* | (2006.01) |
| *A61K 8/19* | (2006.01) |
| *A61K 8/21* | (2006.01) |
| *A61Q 11/00* | (2006.01) |
| *A61Q 13/00* | (2006.01) |
| *A61K 8/24* | (2006.01) |
| *A61K 9/00* | (2006.01) |
| *A61K 9/50* | (2006.01) |
| *A61K 33/44* | (2006.01) |
| *A61Q 3/02* | (2006.01) |
| *A61Q 5/02* | (2006.01) |
| *A61Q 5/06* | (2006.01) |
| *A61K 8/64* | (2006.01) |
| *A61Q 5/12* | (2006.01) |
| *A61Q 19/00* | (2006.01) |
| *A61K 8/87* | (2006.01) |

(52) U.S. Cl.
CPC .............. *A61K 8/11* (2013.01); *A61K 6/0017* (2013.01); *A61K 6/0067* (2013.01); *A61K 6/0073* (2013.01); *A61K 8/19* (2013.01); *A61K 8/21* (2013.01); *A61K 8/24* (2013.01); *A61K 8/64* (2013.01); *A61K 8/87* (2013.01); *A61K 9/0056* (2013.01); *A61K 9/5031* (2013.01); *A61K 9/5089* (2013.01); *A61K 33/06* (2013.01); *A61K 33/16* (2013.01); *A61K 33/44* (2013.01); *A61K 47/02* (2013.01); *A61Q 3/02* (2013.01); *A61Q 5/02* (2013.01); *A61Q 5/06* (2013.01); *A61Q 5/12* (2013.01); *A61Q 11/00* (2013.01); *A61Q 19/00* (2013.01); *A61K 2800/412* (2013.01)

(58) Field of Classification Search
CPC ........ A61K 8/11; A61K 6/0017; A61K 33/06; A61K 33/16; A61K 11/00; A61K 3/02; A61K 5/06; A61K 8/64
See application file for complete search history.

(56) References Cited

U.S. PATENT DOCUMENTS

| | | | |
|---|---|---|---|
| 3,442,842 A | 5/1969 | Bonin | |
| 4,652,441 A | 3/1987 | Okada et al. | |
| 4,711,782 A | 12/1987 | Okada | |
| 4,762,899 A | 8/1988 | Shikinami | |
| 4,891,208 A | 1/1990 | Janoff et al. | |
| 5,614,175 A | 3/1997 | Winston et al. | |
| 5,665,382 A | 9/1997 | Grinstaff et al. | |
| 5,910,492 A | 6/1999 | Hoshino et al. | |
| 5,925,595 A | 7/1999 | Seitz et al. | |
| 6,099,861 A | 8/2000 | DeSenna et al. | |
| 6,534,091 B1 | 3/2003 | Garces et al. | |
| 7,604,940 B1 | 10/2009 | Voss | |
| 8,889,161 B2 * | 11/2014 | Latta | A61K 8/11 424/401 |

(Continued)

FOREIGN PATENT DOCUMENTS

| | | |
|---|---|---|
| CA | 2073685 | 7/1991 |
| CA | 2187768 | 10/1995 |

(Continued)

OTHER PUBLICATIONS

U.S. Appl. No. 16/207,515, filed Dec. 2018, Latta; Mark A, A61K 8/11.*

(Continued)

*Primary Examiner* — Mina Haghighatian
(74) *Attorney, Agent, or Firm* — Vos-IP, LLC

(57) ABSTRACT

A microcapsule composition comprising at least one polymer substantially disposed as a semi-permeable shell around a buffered solution and at least one therapeutic agent, wherein the therapeutic agent permeates the shell, and wherein the composition is suitable for delivery to a mammal. This invention also provides related compositions, products and methods.

13 Claims, 2 Drawing Sheets

(56) References Cited

U.S. PATENT DOCUMENTS

| | | |
|---|---|---|
| 9,498,411 B2 | 11/2016 | Quali |
| 9,689,024 B2 | 6/2017 | Hindson et al. |
| 9,814,567 B2 * | 11/2017 | Peyman .............. A61F 9/00804 |
| 2002/0064541 A1 | 5/2002 | Lapidot et al. |
| 2002/0090398 A1 | 7/2002 | Dunn et al. |
| 2005/0277549 A1 | 12/2005 | Seitz et al. |
| 2007/0275078 A1 | 11/2007 | Morato Riera et al. |
| 2008/0038304 A1 | 2/2008 | Nouvel |
| 2008/0044464 A1 | 2/2008 | Tardi et al. |
| 2008/0103265 A1 | 5/2008 | Schocker |
| 2008/0152598 A1 | 6/2008 | Basic |
| 2008/0175918 A1 | 7/2008 | Laulicht |
| 2010/0272764 A1 | 10/2010 | Latta et al. |
| 2011/0230390 A1 | 9/2011 | Ouali et al. |
| 2018/0200163 A1 * | 7/2018 | Latta ....................... A61K 8/11 |
| 2018/0200164 A1 * | 7/2018 | Latta ..................... A61Q 13/00 |

FOREIGN PATENT DOCUMENTS

| | | | |
|---|---|---|---|
| CA | 2289761 | | 11/1998 |
| CA | 2331465 | | 11/1999 |
| CA | 2247013 | | 3/2000 |
| CA | 2490351 | | 12/2003 |
| CA | 2513483 | | 8/2004 |
| CN | 1131042 | | 9/1996 |
| CN | 1187122 | | 7/1998 |
| CN | 1259028 | | 7/2000 |
| EP | 0174377 | A1 | 3/1986 |
| EP | 0452268 | | 4/2005 |
| JP | S58189031 | | 11/1983 |
| JP | H07502038 | | 3/1995 |
| JP | 10-510550 | | 10/1998 |
| WO | WO1983003061 | | 9/1983 |
| WO | WO9110506 | | 7/1991 |
| WO | WO1993011738 | | 6/1993 |
| WO | WO199059554 | | 11/1995 |
| WO | WO 96/39134 | | 12/1996 |
| WO | WO 2004/022220 | | 3/2004 |
| WO | WO2007009023 | | 1/2007 |

OTHER PUBLICATIONS

U.S. Appl. No. 16/207,545, filed Dec. 2018, Latta; Mark A, A61K 8/11.*

International Search Report issued in International Application No. PCT/US2013/059513 dated Apr. 24, 2014.

Kiyoyama et al., "Preparation of Cross-linked Microcapsules Entrapping Inorganic Salt by In-Situ Polymerization in (W/O/W) emulsion System", J Chem Eng Japan 34: 36-42 (2001).

Lowenstam et al., Science 188: 363 (1975).

Tung, Ming S., CE2, Amorphous Calcium Phosphates for Tooth Mineralization, Sep. 2004, vol. 25, No. 9 , American Dental Association Foundation.

Charig, Andrew, CE 3, Enamel Mineralization by Calcium-containing Bicarbonete Toothpastes: Assessment by Various Techniques, Compendium, Sep. 2004, vol. 25, No. 9.

Litkowski, Leonard J., CE4, Intraoral Evaluation of Mineralization of Cosmetic Defects by a Toothpaste Containing Calcium, Fluoride, and Sodium Bicarbonate, Compendium, Sep. 2004, vol. 25, No. 9.

Xu, HHK, Strong Nanocomposites with Ca PO4, and F Release for Caries Inhibition, Critical Reviews in Oral Biology & Medicine, Jan. 2009.

Rover!, Norberto, Surface Enamel Remineralization: Biomimetic Apatite Nanocrystals and Fluoride Ions Different 'Effects, vol. 2009, Article ID 746383, Journal of Nanomatrials.

Lei, Y., in Vitro Degradation of novel Biocative Polycarprolactone—20% Tricalcium Phosphate Composite Scaffolds for Bone Engineering, Materials and Science and Engineering, vol. 27, Issue 2, Mar. 2007.

Lasic, "Novel applications of liposomes", Trends in Biotechnology, vol. 16 Issue 7, Jul. 1, 1998, 307-321.

* cited by examiner

Epifluorescent microscopic images of a microcapsule containing FITC-labeled lysozyme in PBS. The imaged microcapsule is approximately 7 micrometers in size.

Confocal fluorescent imaging scan of a microcapsule containing FITC-labeled lysozyme in PBS. The imaged microcapsule is approximately 7 micrometers in size.

BUFFERED MICROENCAPSULATED COMPOSITIONS AND METHODS

This application is a divisional of U.S. patent application Ser. No. 13/619,128 which was filed with the U.S. Patent and Trademark Office on Sep. 14, 2012, which is a continuation-in-part of U.S. application Ser. No. 12/768,696, filed Apr. 27, 2010, which claims priority of U.S. Provisional Application No. 61/172,939, filed Apr. 27, 2009, the contents of which are incorporated herein by reference in their entirety.

BACKGROUND OF THE INVENTION

The present invention is directed to compositions, compounds and methods for the mineralization of various physiological tissues, primarily of bone and teeth. Mineralized connective tissue or tissues include teeth, bone, and various connective tissues such as collagen, cartilage, tendons, ligaments and other dense connective tissue and reticular fibers (that contains type III collagen) of a mammal, including a human being. For purposes of definition in this specification, "mineralized tissue" shall mean bone and teeth specifically. Each of the terms "mineralization", "tissue mineralization", used interchangeably herein, means a process in which crystals of calcium phosphate are produced by bone-forming cells or tooth-forming cells and laid down in precise amounts within the fibrous matrix or scaffolding of the mineralized tissue as defined hereinabove.

Calcium phosphates are a class of minerals containing, but not limited to, calcium ions together with orthophosphates, metaphosphates and/or pyrophosphates that may or may not contain hydrogen or hydroxide ions.

For purposes of definition in this specification, "remineralization" is the process of restoring minerals, in the form of mineral ions, to the hydroxyapatite latticework structure of a tooth. As used herein, the term "remineralization" includes mineralization, calcification, re-calcification and fluoridation as well as other processes by which various particular ions are mineralized to the tooth. The term "teeth" or "tooth" as used herein includes the dentin, enamel, pulp and cementum of a tooth within the oral cavity of an animal, including a human being.

In certain embodiments, the present invention provides methods for whitening the surface of a tooth material by using the compositions of the invention. For purposes of definition in this specification, as referred to herein, a "tooth material" refers to natural teeth, dentures, dental plates, fillings, caps, crowns, bridges, dental implants, and the like, and any other hard surfaced dental prosthesis either permanently or temporarily fixed to a tooth within the oral cavity of an animal, including a human being. As used herein, the terms "whitening" and "tooth whitening" used interchangeably, refer to a change in the visual appearance of a tooth as defined herein, preferably such that the tooth has a brighter shade or luster.

Conditions of the Bone

No currently practiced therapeutic strategy involves methods or compositions that sufficiently stimulate or enhance the growth of new bone mass. The present invention provides compositions, products and methods which serve to increase bone mineralization at localized sites or remineralization of teeth directly in the oral cavity, and thus may be utilized in conjunction with treatments of a wide variety of conditions where it is desired to increase bone or tissue mass as a result of any condition which can be improved by bioavailability of physiological salts, particularly of calcium and phosphate.

Certain changes in bone mass occur over the life span of an individual. After about the age of 40 and continuing to the last stages of life, slow bone loss occurs in both men and women. Loss of bone mineral content can be caused by a variety of conditions, and may result in significant medical problems. If the process of tissue mineralization is not properly regulated, the result can be too little of the mineral or too much—either of which can compromise bone health, hardness and strength. A number of bone growth disorders are known which cause an imbalance in the bone remodeling cycle. Chief among these are metabolic bone diseases such as osteoporosis, osteoplasia (osteomalacia), chronic renal failure and hyperparathyroidism, which result in abnormal or excessive loss of bone mass known as osteopenia. Other bone diseases, such as Paget's disease, also cause excessive loss of bone mass at localized sites.

Osteoporosis is a structural deterioration of the skeleton caused by loss of bone mass resulting from an imbalance in bone formation, bone resorption, or both. Bone resorption is the process by which osteoclasts break down bone and release the minerals, resulting in a transfer of calcium from bone fluid to the blood. Bone resorption dominates the bone formation phase, thereby reducing the weight-bearing capacity of the affected bone. In a healthy adult, the rate at which bone is formed and resorbed is tightly coordinated so as to maintain the renewal of skeletal bone. However, in osteoporotic individuals, an imbalance in these bone remodeling cycles develops which results in both loss of bone mass and in formation of micro-architectural defects in the continuity of the skeleton. These skeletal defects, created by perturbation in the remodeling sequence, accumulate and finally reach a point at which the structural integrity of the skeleton is severely compromised and bone fracture is likely. Although this imbalance occurs gradually in most individuals as they age, it is much more severe and occurs at a rapid rate in postmenopausal women. In addition, osteoporosis also may result from nutritional and endocrine imbalances, hereditary disorders and a number of malignant transformations.

Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing billions of dollars annually in the United States. In addition to health care related costs, long-term residential care and lost working days add to the financial and social costs of this disease. Worldwide, approximately 75 million people are at risk for osteoporosis.

The frequency of osteoporosis in the human population increases with age, and among Caucasians is predominant in women, who comprise approximately 80% of the osteoporosis patient pool in the United States. In addition in women, another phase of bone loss occurs possibly due to postmenopausal estrogen deficiencies. During this phase of bone loss, women can lose an additional 10% in the cortical bone and 25% from the trabecular compartment. The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Patients suffering from chronic renal (kidney) failure almost universally suffer loss of skeletal bone mass, termed renal osteodystrophy. While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Osteoplasia, also known as osteomalacia ("soft bones"), is a defect in bone mineralization (e.g., incomplete mineralization), and classically is related to vitamin D deficiency (1,25-dihydroxy vitamin D3). The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) is known to cause malabsorption of calcium, leading to abnormal bone loss. In children, hyperparathyroidism can inhibit growth, in adults the skeleton integrity is compromised and fracture of the ribs and vertebrae are characteristic. The parathyroid hormone imbalance typically may result from thyroid adenomas or gland hyperplasia, or may result from prolonged pharmacological use of a steroid. Secondary hyperparathyroidism also may result from renal osteodystrophy. In the early stages of the disease, osteoclasts are stimulated to resorb bone in response to the excess hormone present. As the disease progresses, the trabecular bone ultimately is resorbed and marrow is replaced with fibrosis, macrophages and areas of hemorrhage as a consequence of microfractures, a condition is referred to clinically as osteitis fibrosa.

Paget's disease (osteitis deformans) is a disorder currently thought to have a viral etiology and is characterized by excessive bone resorption at localized sites which flare and heal but which ultimately are chronic and progressive, and may lead to malignant transformation. The disease typically affects adults over the age of 25.

Although osteoporosis has been defined as an increase in the risk of fracture due to decreased bone mass, none of the presently available treatments for skeletal disorders can substantially increase the bone density of adults. A strong perception exists among physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity, particularly in weight-bearing activities, with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer. High doses of dietary calcium with or without vitamin D have also been suggested for postmenopausal women. However, ingestion of high doses of calcium can often have unpleasant gastrointestinal side effects, and serum and urinary calcium levels must be continuously monitored.

Other therapeutics which have been suggested include calcitonin, bisphosphonates, anabolic steroids and sodium fluoride. Such therapeutics however, have undesirable side effects, for example, calcitonin and steroids may cause nausea and provoke an immune reaction, bisphosphonates and sodium fluoride may inhibit repair of fractures, even though bone density increases modestly, which that may prevent their usage.

The above disorders are examples of conditions that may lead to bone fractures, fissures or splintering of the bones in the individuals who suffer from a given disorder. Current therapeutic methods are insufficient to treat the disorders leaving a need for improved treatments of bone fractures when they occur in the individual. The present invention provides improved compositions, products and methods for locally treating bone fractures, fissures, splintering and similar breakages of the bone, or by strengthening decomposed bone tissue by increasing the mechanism of mineralization of the bone. It is conceivable that the current invention also causes mineralization of the surrounding connective tissue, such as collagen, cartilage, tendons, ligaments and other dense connective tissue and reticular fibers.

The Oral Cavity

With respect to tissue decomposition in the oral cavity, it is commonly known in the dental art that certain kinds of tooth decomposition and decay that occurs over time in the mouth is initiated by acid etching of the tooth enamel with the source of the acid being a metabolite resulting from bacterial and enzymatic action on food particles in the oral cavity. It is generally understood that plaque, a soft accumulation on the tooth surface consisting of an organized structure of microorganisms, proteinaceous and carbohydrate substances, epithelial cells, and food debris, is a contributory factor in the development of various pathological conditions of the teeth and soft tissue of the oral cavity. The saccharolytic organisms of the oral cavity which are associated with the plaque, cause a demineralization or decalcification of the tooth beneath the plaque matrix through metabolic activity which results in the accumulation and localized concentration of organic acids. The etching and demineralization of the enamel may continue until they cause the formation of dental caries and periodontal disease within the oral cavity.

Teeth are cycled through periods of mineral loss and repair also as a result of pH fluctuations in the oral cavity. The overall loss or gain of mineral at a given tooth location determine whether the carious process will regress, stabilize or advance to an irreversible state. Numerous interrelated patient factors affect the balance between the remineralization and demineralization portions of this cycle and include oral hygiene, diet, and the quantity and quality of saliva. At the most extreme point in this process, a restoration will be required to repair the tooth.

Methods for the prevention and reduction of plaque and tooth decay within the oral cavity commonly involve the brushing of the teeth using toothpastes; mechanical removal of the plaque with dental floss; administration and rinsing of the oral cavity with mouthwashes, dentifrices, and antiseptics; remineralization and whitening of the teeth with fluoride agents, calcium agents and whitening agents, and various other applications to the oral cavity. Still missing in the field is a delivery system for the remineralization of teeth that would address the challenges of demineralization facing the teeth continually in the oral cavity.

A tooth that has reached an advanced stage of decay often requires installation of a dental restoration within the mouth. Half of all dental restorations fail within 10 years, and replacing them consumes 60% of the average dentist's practice time. Current dental materials are challenged by the harsh mechanical and chemical environment of the oral cavity with secondary decay being the major cause of failure. Development of stronger and longer-lasting biocompatible dental restorations by engineering novel dental materials or new resin systems, enhancing existing materials, and incorporating bioactive agents in materials to combat microbial destruction and to sustain the harsh mechanical and chemical environment of the oral cavity continues to be desired.

Despite numerous preventive oral health strategies, dental caries remains a significant oral health problem. More than 50% of children aged 6-8 will have dental caries and over 80% of adolescents over age 17 will have experienced the disease. Caries is also seen in adults both as a primary disease and as recurrent disease in already treated teeth. Advances in diagnosis and treatment have led to non-invasive remineralizing techniques to treat caries. However mechanical removal of diseased hard tissue and restoration and replacement of enamel and dentin is still the most widely employed clinical strategy for treating primary caries, restoring function to the tooth and also blocking further decay. In addition, nearly 50% of newly placed restorations are replacement of failed restorations. Clearly, restorative materials are a key component of treating this widespread disease.

The selection of a restorative material has significantly changed in recent years. While dental amalgam is still considered a cost effective material, there is a growing demand for tooth colored alternatives that will provide the same clinical longevity that is enjoyed by dental amalgam. The use of composite resins has grown significantly internationally as a material of choice for replacing amalgam as a restorative material for posterior restorations. This demand is partially consumer driven by preference for esthetic materials and the concerns regarding the mercury content of amalgam. It is also driven by dentists recognizing the promise of resin-based bonded materials in preserving and even supporting tooth structure. Numerous studies have suggested that bonding the restoration to the remaining tooth structure decreases fracture of multi-surface permanent molar preparations. Unfortunately, posterior teeth restored with direct resin restorative materials have a higher incidence of secondary caries. This has led to shorter clinical service and narrower clinical indications for composite resin materials compared to amalgam.

The most frequently cited reason for restoration replacement is recurrent decay around or adjacent to an existing restoration. It is likely that fracture at the margin due to polymerization shrinkage can lead to a clinical environment at the interface between a restoration and the tooth that collects dental plaque and thus promotes decay. Therefore, developing dental materials with anti-caries capability is a very high priority for extending the longevity of restorations.

Tooth Remineralization

Although natural remineralization is always taking place in the oral cavity, the level of activity varies according to conditions in the mouth as discussed. Incorporation of fluoride during the remineralization process has been a keystone for caries prevention. The effectiveness of fluoride release from various delivery platforms, including certain dental restorative materials has been widely demonstrated. It is commonly accepted that caries prevention from fluoride is derived from its incorporation as fluorapatite or fluoride enriched hydroxyapatite in the tooth mineral thereby decreasing the solubility of tooth enamel. More recently, anti-caries activity has been demonstrated using the strategy of increasing solution calcium and phosphate concentrations to levels that exceed the ambient concentration in oral fluids. In order for fluoride to be effective at remineralizing previously demineralized enamel, a sufficient amount of calcium and phosphate ions must be available. For every two (2) fluoride ions, ten (10) calcium ions and six (6) phosphate ions are required to form a cell of fluorapatite ($Ca_{10}(PO_4)_6F_2$). Thus the limiting factor for net enamel remineralization is the availability of calcium and fluoride in saliva.

The low solubility of calcium phosphates has limited their use in clinical delivery platforms, especially when in the presence of fluoride ions. These insoluble phosphates can only produce available ions for diffusion into the enamel in an acidic environment. They do not effectively localize to the tooth surface and are difficult to apply in clinically usable forms. Because of their intrinsic solubility, soluble calcium and phosphate ions can only be used at very low concentrations. Thus they do not produce concentration gradients that drive diffusion into the subsurface enamel of the tooth. The solubility challenge is exacerbated by the even lower solubility of calcium fluoride phosphates.

Several commercially available approaches exist using calcium and phosphate preparations that have been commercialized into various dental delivery models. These have been reportedly compounded to overcome the limited bioavailability of calcium and phosphate ions for the remineralization process. The first technology uses casein phosphopeptide (CCP) stabilized with amorphous calcium phosphate (ACP) (RECALDENT® CCP-ACP of Cadbury Enterprises Pte. Ltd.). It is hypothesized that the casein phosphopeptide can facilitate the stabilization of high concentrations of ionically available calcium and phosphate even in the presence of fluoride. This formulation binds to pellicle and plaque and while the casein phosphopeptide prevents the formation of dental calculus, the ions are available to diffuse down the concentration gradient to subsurface enamel lesions facilitating remineralization. As compared to the CCP-ACP, in the composition of the invention, biologically available ions are available due to the fact that the salts are already solvated in the microcapsule of the invention. Amorphous calcium phosphate is not soluble in water or saliva. Although the manufacturer claims release of bioavailable ions from amorphous calcium phosphate, it is not as a result of the dissolution of the complex. A second technology (ENAMELON®) uses unstabilized amorphous calcium phosphate. Calcium ions and phosphate ions are introduced as a dentifrice separately in a dual chamber device forming amorphous calcium phosphate in-situ. It is proposed that formation of the amorphous complex promotes remineralization. A third approach uses a so-called bioactive glass (NOVAMIN® of NovaMin Technology Inc.) containing calcium sodium phosphosilicate. It is proposed that the glass releases calcium and phosphate ions that are available to promote remineralization. More recently dental composite formulations have been compounded using zirconia-hybridized ACP that may have the potential for facilitating clinical remineralization.

While the Recaldent® and Enamelon® preparations have both in-situ and in-vivo evidence suggesting enhanced remineralization, these are topically applied and do not specifically target the most at risk location for recurrent caries at the tooth restoration interface. While the bioactive glass and the zirconia-hybridized-ACP filler technologies have potential, they are relatively inflexible in terms of the range of formulations in which they might be used due to the challenges of dealing with brittle fillers and some of the limitations on controlling filler particle size.

Another approach taken to decrease caries in the oral cavity is the limiting of demineralization of enamel and bone by drinking water fluoridation. It has been shown that the fluoride contained in drinking water incorporates to some extent into hydroxyapatite, the major inorganic component of enamel and bone. Fluoridated hydroxyapatite is less susceptible to demineralization by acids and is thus seen to resist the degradation forces of acidic plaque and pocket metabolites. In addition, fluoride ion concentration in saliva is increased through consumption of fluoridated drinking water. Saliva thus serves as an additional fluoride ion reservoir and in combination with buffering salts naturally found in salivary fluid, fluoride ions are actively exchanged on the enamel surface, further offsetting the effects of demineralizing acid metabolites.

Notwithstanding the established benefits of fluoride treatment of teeth, fluoride ion treatment can result in irregular spotting or blotching of the teeth depending on the individual, whether administered through drinking water or by topically applied fluoride treatment. This effect is known to be both concentration related and patient specific. In addition, the toxicology of fluoride is being studied as to its long term effect on human health. Desired is a targeted approach of fluoridation in the oral cavity.

Another approach to limiting the proliferation of microflora in the oral environment is through topical or systematic application of broad-spectrum antibacterial compounds. Reducing the number of oral microflora in the mouth results in a direct reduction or elimination of plaque and pocket accumulation together with their damaging acidic metabolite production. The major drawback to this particular approach is that a wide variety of benign or beneficial strains of bacteria are found in the oral environment which may be killed by the same antibacterial compounds in the same manner as the harmful strains. In addition, treatment with antibacterial compounds may select for certain bacterial and fungi, which may then become resistant to the antibacterial compound administered and thus proliferate, unrestrained by the symbiotic forces of a properly balanced microflora population. Thus the application or administration of broad-spectrum antibiotics alone is ill-advised for the treatment of caries and a more specific, targeted approach is desired.

Tooth Whitening

Cosmetic dental whitening or bleaching has become extremely desirable to the general public. Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as eating, chewing, or drinking certain foods and beverages (in particular coffee, tea, and red wine) and smoking or other oral use of tobacco products cause undesirable staining of surfaces of teeth. Extrinsic staining of the acquired pellicle arises as a result of compounds such as tannins and polyphenolic compounds which become trapped in and tightly bound to the proteinaceous layer on the surfaces of teeth. This type of staining can usually be removed by mechanical methods of tooth cleaning. In contrast, intrinsic staining occurs when staining compounds penetrate the enamel and even the dentin or arise from sources within the tooth. The chromogens or color causing substances in these materials become part of the pellicle layer and can permeate the enamel layer. Even with regular brushing and flossing, years of chromogen accumulation can impart noticeable tooth discoloration. Intrinsic staining can also result from microbial activity, including that associated with dental plaque. This type of staining is not amenable to mechanical methods of tooth cleaning and chemical methods are required.

Without specifically defining the mechanism of action of the present invention, the compositions, products and methods of the present invention enable the precipitation of salts onto the surfaces of the teeth in the oral cavity and make the salts available for adherence to the tooth surface and remineralization of the teeth. The mineralizing salts are deposited in the interstitial spaces of the teeth, making the teeth smoother, increasing the reflection of light from the surface of the teeth and thereby giving the teeth a brighter, more lustrous appearance and whiter visual effect.

Tooth whitening compositions generally fall into two categories: (1) gels, pastes, varnishes or liquids, including toothpastes that are mechanically agitated at the stained tooth surface in order to affect tooth stain removal through abrasive erosion of stained acquired pellicle; and (2) gels, pastes, varnishes or liquids that accomplish the tooth whitening effect by a chemical process while in contact with the stained tooth surface for a specified period, after which the formulation is removed. In some cases, the mechanical process is supplemented by an auxiliary chemical process which may be oxidative or enzymatic. Initially, tooth whitening had been performed at the dentist's office. Less expensive at-home dental whitening kits have become available, such as whitening strips and whitening trays that come in either single compartment or dual compartment systems.

Both in-office and at-home tooth whitening typically involves the application of a peroxide containing composition to the surface of the tooth to achieve the desired whitening effect. The majority of most in-office and at-home tooth whitening compositions act by oxidation. These compositions are applied directly by a patient in a tooth-bleaching tray, held in place in the mouth for contact times, sometimes for periods of half an hour several times per day; or of greater than 60 minutes per day, and sometimes as long as 8 to 12 hours. The slow rate of bleaching is, in large part, the consequence of formulations that are developed to maintain stability of the oxidizing composition. Aqueous tooth whitening gels have proven desirable due to the hydrating effects on the structure of the tooth, reducing the likelihood of tooth sensitivity.

The most commonly used oxidative compositions contain the hydrogen peroxide precursor carbamide peroxide which is mixed with an anhydrous or low-water content, hygroscopic viscous carrier containing glycerine and/or propylene glycol and/or polyethylene glycol. When contacted by water, carbamide peroxide dissociates into urea and hydrogen peroxide. The latter has become the tooth bleaching material of choice due to its ability to whiten teeth faster than higher concentrations of carbamide peroxide.

An alternative source of hydrogen peroxide is sodium percarbonate and this has been used in a silicone polymer product that is painted onto the teeth forming a durable film for overnight bleaching procedures. The peroxide is slowly released for up to 4 hours.

Associated with the slow rate of bleaching-in the hygroscopic carrier, the currently available tooth-bleaching compositions cause tooth sensitization in over 50% of patients. Tooth sensitivity is believed to result from the movement of fluid through the dentinal tubes toward nerve endings in the tooth. This movement is enhanced by the carriers for the carbamide peroxide. It has been determined that glycerine, propylene glycol and polyethylene glycol can each give rise to varying amounts of tooth sensitivity following exposure of the teeth to heat, cold, overly sweet substances, and other causative agents.

Hydrogen peroxide tooth bleaching formulations have limitations in addition to tooth sensitivity. Until recent years, stable aqueous hydrogen peroxide tooth bleaching gels have been virtually non-existent. Hydrogen peroxide is a powerful oxidizing agent and an unstable compound that decomposes readily over time into water and oxygen. Certain chemical and physical influences in the oral cavity can accelerate the rate of decomposition and need to be controlled for a stable tooth whitening gel to exist. Temperature, pH and errant metal ions all have a profound effect on the decomposition of hydrogen peroxide, particularly in an aqueous formula.

One advantage of the compositions of the invention is the decrease or elimination of tooth sensitivity of the patient. When used in conjunction with current tooth bleaching products, the microcapsules of the invention release salt ions that precipitate as salts in the oral cavity and mineralize the open dentin tubules of the teeth thereby decreasing tooth sensitivity to the oxidative tooth bleaching product.

Whitening systems on the market include two-part systems that require mixing of the components upon administration and single part compositions that are faster and easier to administer and generally preferred for in-office bleaching by dentists. Two-part systems include products such as dual barrel syringes, liquid hydrogen peroxide/powder systems and whitening strips. Single component tooth bleaching compositions prefer room temperature storage conditions in order to eliminate costly and inconvenient storage problems. The pH of an aqueous hydrogen peroxide tooth whitening composition also has great bearing on the stability of the formulation. The two-part systems demonstrate superior shelf life stability. Formulations that contain hydrogen peroxide solutions are strongly acidic and maintain their stability in acidic pH formulas. Stable aqueous hydrogen peroxide tooth whitening gels can be formulated in the acid pH range. However, bleaching compositions in the acidic pH range (pH 2.0-5.5) are prone to the demineralization of dental enamel by the solubilizing of calcium ions from the tooth surface. This reduction in surface enamel leads to tooth sensitivity and discomfort for the patient. By incorporating the compositions of the invention into tooth bleaching products or utilizing them in conjunction with tooth bleaching products, the microcapsules of the invention can modify the pH level in the oral cavity to cause acceleration of the bleaching process.

Many of the available products are time-consuming and limited in their effectiveness and subject the user to various physical discomforts. More importantly, it has been shown that prolonged exposure of teeth to whitening compositions, as practiced at present, has a number of adverse effects in addition to that of tooth sensitivity. Over time, any of the peroxides known in the art to achieve a desired tooth bleaching effect will function as calcium chelating agents. Other examples of chelation agents often found in tooth whitening products include EDTA and its salts, citric acid and its salts, gluconic acid and its salts, alkali metal pyrophosphates and alkali metal polyphosphates. Solubilization of calcium from the enamel layer can occur at a pH less than 5.5 with associated demineralization. The chelating agents will penetrate the intact enamel and dentin so as to reach the pulp chamber of a vital tooth thereby risking damage to pulpal tissue. Other adverse effects include dilution of the bleaching compositions with saliva in the oral cavity with resulting leaching from the dental tray and subsequent digestion by the user.

It has been shown that the rate of whitening can be increased by increasing the temperature of the hydrogen peroxide system, where increase of 10.degree. C. can double the rate of reaction. Consequently, there exist a number of procedures that utilize high-intensity light to raise the temperature of the hydrogen peroxide to accelerate the rate of bleaching of the teeth. Other approaches to heating the hydrogen peroxide have been described such as the heating of dental instruments. Contemporary approaches and literature have focused on accelerating peroxide bleaching with simultaneous illumination of the anterior teeth with various sources having a range of wavelengths and spectral power, for example, halogen curing lights, plasma arc lamps, lasers and light-emitting diodes. Some products that are used in light activated whitening procedures contain ingredients that serve as photosensitizers that claim to aid the energy transfer from the light to the peroxide gel and are often colored materials, for example carotene and manganese sulfate. However, excessive heating can cause irreversible damage to the dental pulp. In addition, the literature for in vitro and clinical studies and actual results demonstrate that the actual effect of light on tooth whitening is limited, conflicting and controversial.

There is thus a need for improved compositions, methods and products that overcome the limitations of the prior art. The challenge remains to create a tooth whitening and remineralization technology platform for incorporating stable and effective tissue remineralization ions that can be incorporated into a myriad of dental materials and variety of products. Such a delivery platform would facilitate the formulation of dental products capable of remineralization of the teeth. The compositions, products and methods of the current inventions as described herein satisfy these and other needs. The ultimate impact is a reduction in recurrent caries, the most prevalent reason for restoration replacement; whitening of the teeth; and resulting improvement in overall strength and health of the teeth in the oral cavity.

There exists a broad need for improved compositions and methods useful for therapeutic agent delivery. In particular, there is a need for an improved microcapsule-based technology for delivering therapeutic agents to diverse tissue types in a stable and time-controlled manner.

SUMMARY OF THE INVENTION

In accordance with the description herein and desire to provide improved therapeutic products, the present invention provides compositions and methods that deliver a buffered therapeutic agent in a controlled fashion. Also presented are methods for using such compositions in the treatment and prevention of a wide variety of conditions resulting from microorganisms. The invention also provides compositions and products for antimicrobial coatings. More particularly, the present invention provides a composition comprising buffered solutions of therapeutic agents encapsulated in a semi-permeable polymer shell that allows the release of therapeutic agents to be delivered to a patient. The microcapsules can be incorporated into a variety of products as discussed herein, and can be prepared by any generally known microencapsulation method, but preferably by surfactant-free inverse emulsion. More particularly, the invention includes a composition containing polymer microencapsulated solutions of buffered therapeutic agents. Further, the rate of release of the therapeutic agent from the microcapsules can be designed in a single type of microcapsule and in a product containing a number of different types of microcapsules. This results in controlled time release of the agent and thereby a therapeutic effect over a prolonged period of time.

DETAILED DESCRIPTION OF THE INVENTION

This invention provides buffered, as well as non-buffered, microcapsule compositions for delivering therapeutic agents to a mammal, preferably a human. The non-limiting description below sets forth various embodiments of the subject compositions, and methods of making and using same.
Production of Microcapsules
Microencapsulation In a preferred embodiment, the composition of the invention is formed by combining a buffered solution, therapeutic agent, oil-soluble emulsifying agent and at least one type of polymer which, when combined and upon mixing or agitation, form the microcapsules of the invention. As used herein, the term "microcapsules" includes tiny particles or droplets surrounded by a coating to give small capsules having useful properties. Microcapsules are sometimes referred to as microspheres, though a microcapsule of the invention need not be spherical in shape. The material inside the microcapsule shall be referred to herein by the synonymous terms "core" and "internal phase", and the material surrounding the core is referred to herein by the synonymous terms "shell", "wall", "coating", "membrane" and "exterior phase." The shell need not be completely or uniformly placed around the core of the microcapsule, as long as substantially all of the core is surrounded by a polymer shell, as will be described further herein.

Preferably, the microcapsules of the invention have a diameter range of between 100 nanometers and 3 millimeters. More preferably, the size of the microcapsules is between 1 micron and 1 mm. In general, the preferable size of the microcapsule will be governed by the desired end use application. One parameter used to control the size of the microcapsules is by the amount and force of mixing or agitation of the emulsion. Other parameters to control the size of the microcapsules and components of the microcapsules will be discussed further below. The size of the instant microcapsules can be optimized so that a sufficient number of microcapsules are available to affect a therapeutic response.

Methods for constructing microcapsules may be physical or chemical. Physical methods include pan coating, air-suspension coating, centrifugal extrusion, vibrational nozzle and spray-drying. Chemical methods include polymerization such as interfacial polymerization, in-situ polymerization and matrix polymerization. In interfacial polymerization, at least two monomers are dissolved separately in immiscible liquids. Upon interface between the liquids, rapid reaction occurs, creating a thin shell or wall of the microcapsule. In-situ polymerization is the direct polymerization of a single monomer carried out on the particle's surface. In matrix polymerization, a core material is embedded during formation of the microcapsule. Microcapsules might also be constructed by using sol-gel techniques, by aqueous or organic solution precipitation synthesis methods, complex coacervation, and by other methods known in the art.

Figure 1:
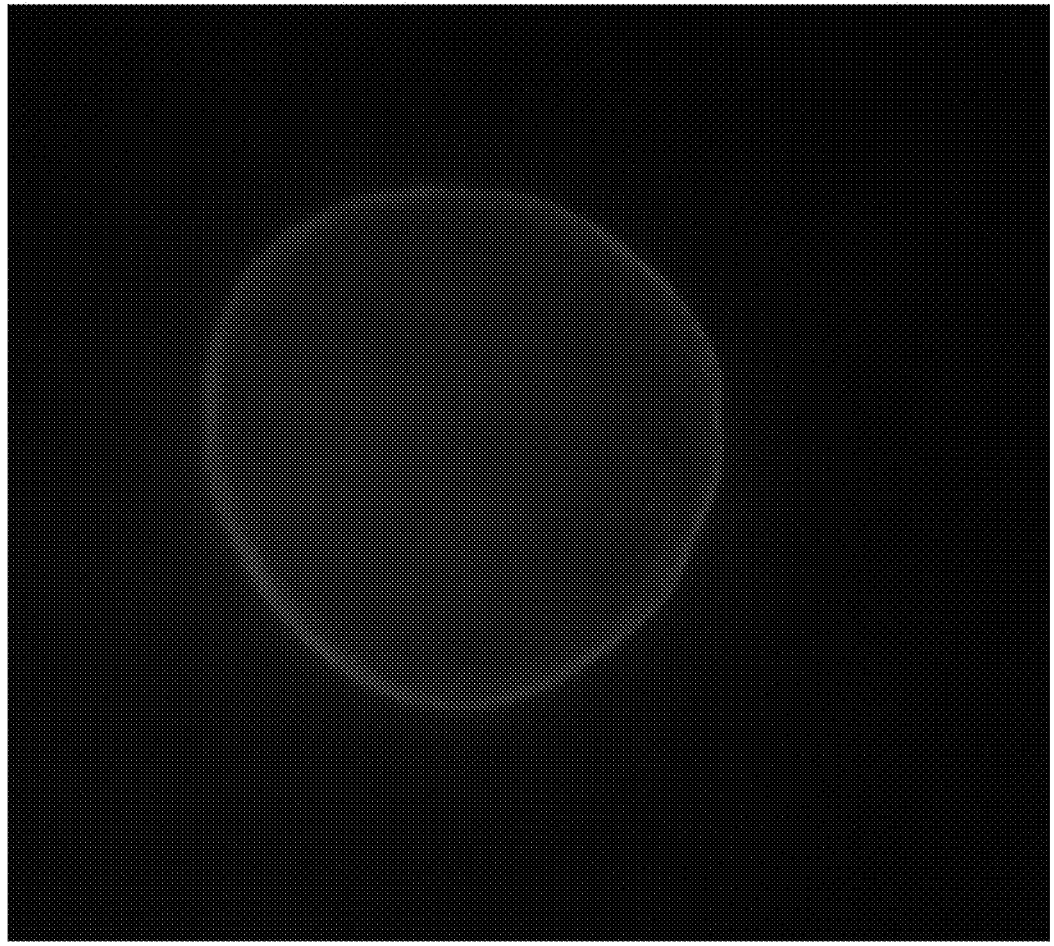
FIG. 1 is an epifluorescent microscopic image of a microcapsule containing FITC-labeled lysozyme in PBS. The imaged microcapsule is approximately 7 micrometers in size.
Figure 2:
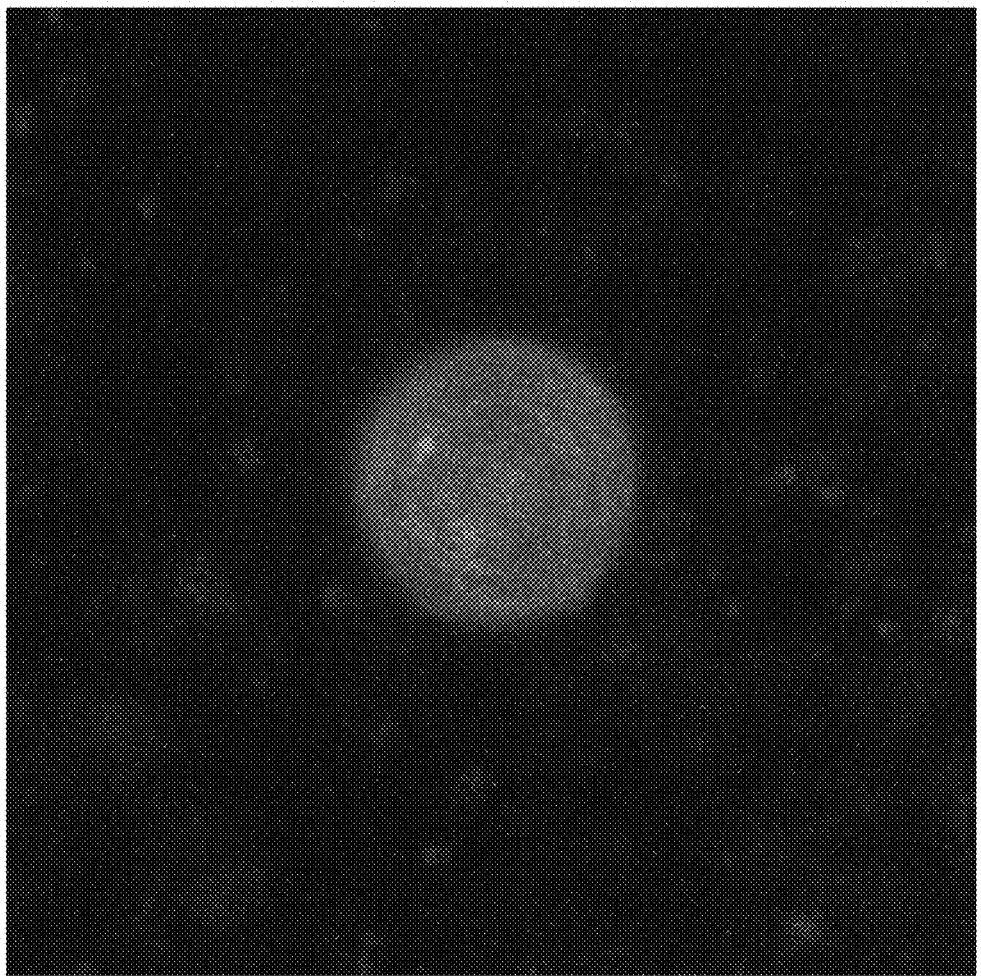
FIG. 2 is a confocal fluorescent imaging scan of a microcapsule containing FITC-labeled lysozyme in PBS. The imaged microcapsule is approximately 7 micrometers in size. Without the use of a buffer solution, the lysozyme denatures and fluorescence is not observed.

A preferred method of preparing the instant microcapsules is a synthesis to generate microcapsules containing buffer solutions of therapeutic agents, and in particular, antimicrobial agents. In order to encapsulate buffered solutions of biologically active additives in a microcapsule, a surfactant-free inverse emulsion of water in oil is preferably used. Any continuous oil phase can be used for the process of the invention. In one embodiment, hydrophobic oils are used as the continuous oil phase within the process with an emulsifying agent that serves to sterically stabilize the dispersed phase. One preferred oil phase of the invention is methyl benzoate. FIG. 1 is an epifluorescent microscopic image of a microcapsule containing FITC-labeled lysozyme in PBS. The imaged microcapsule is approximately 7 micrometers in size. FIG. 2 is a confocal fluorescent imaging scan of a microcapsule containing FITC-labeled lysozyme in PBS. The imaged microcapsule is approximately 7 micrometers in size.

A standard emulsion uses a surfactant to stabilize a dispersed droplet, whereas the present preferred method uses an emulsifying agent in a continuous oil phase to sterically stabilize the dispersed water droplets in order to allow an interfacial polymerization to occur. This causes an effective synthesis of polymer shells around the buffered therapeutic agent solution in the dispersed phase. The amphiphilic character of surfactants causes interference with the polymerization that needs to occur at the interface of the dispersed phase and the continuous phase that is necessary to generate a capsule. A surfactant also presents a problem in its affinity for ions. The polar hydrophilic head group could be attracted to certain types of the therapeutic agents or the ions contained in the capsule for buffering the biologically active additive. The presence of a surfactant decreases the percentage of, for example, ionic therapeutic agents that are truly bioavailable, effectively behaving as a chelation agent inactivating the release of the therapeutic agent from the capsule if the therapeutic agent is ionic in nature. Consequently, surfactant-free inverse emulsion interfacial polymerization is preferred as the method for forming the instant microcapsules of the invention.

Emulsifying Agents

The emulsifying agents preferred in the microcapsules of the invention are different from surfactants in that the emulsifying agents exclusively partition into the oil phase and are not surface active. Inherent in the concept of using surfactant-free inverse emulsions is that water droplets can be disrupted into small droplets, the size and size distribution of which are dependent on the form and amount of input energy, and the droplets formed survive transiently due to a rather sluggish growth rate. Although surfactant-free emulsions have been frequently applied in solvent extraction, emulsion polymerization, and food production such as oil-and-vinegar dressing production, very little attention has been paid to its fundamental properties for use in microencapsulating buffered aqueous therapeutic agent solution systems. The emulsifying agent sterically stabilizes droplets without interfering with interfacial polymerization.

Polymers

The microcapsules of the invention contain a shell comprised of at least one polymer, preferably with the shell being semi-permeable to particular therapeutic agents, whether in buffered solutions. As used herein, the terms "polymer" and "polymers" are intended to connote precursor polymer molecules having a preferable size in the range of 1,000 to 50,000 g/mole; more preferably from 1,500 to 20,000 g/mole; and more preferably from 1,500 to 8,000 g/mole. Larger polymers can be used, as well as smaller oligomers or pre-polymers, but the molecular weight of the polymer is controlled for practical uses in the desired product applications. Conceivably, monomers can be used as well in the method of the invention. A number of polymers can be combined into one microcapsule in order to produce an end use product having particularly desired release characteristics of the core components.

In one embodiment of the invention, the microcapsule shell is designed with limited or substantially no permeability depending on its desired application. The impermeable shell is formed during synthesis by selecting particular polymers known to be impermeable to the particular therapeutic agents in the desired end use application. Such microcapsules may, for example, be synthesized for "burst" application as discussed herein.

Many classes of polymers can be used in the scope of the invention and the choice depends on the specific desired properties. Examples include, but are not limited to, acrylic polymers, alkyl resins, aminoplasts, coumarone-indene resins, epoxy resins, fluoropolymers, phenolic resins, polyacetals, polyacetylenes, polyacrylics, polyalkylenes, polyalkenylenes, polyalkynylenes, polyamic acids, polyamides, polyamines, polyanhydrides, polyarylenealkenylenes, polyarylenealkylenes, polyarylenes, polyazomethines, polybenzimidazoles, polybenzothiazoles, polybenzoxazinones, polybenzoxazoles, polybenzyls, polycarbodiimides, polycarbonates, polycarboranes, polycarbosilanes, polycyanurates, polydienes, polyester-polyurethanes, polyesters, polyetheretherketones, polyether-polyurethanes, polyethers, polyhydrazides, polyimidazoles, polyimides, polyimines, polyisocyanurates, polyketones, polyolefins, polyoxadiazoles, polyoxides, polyoxyalkylenes, polyoxyarylenes, polyoxymethylenes, polyoxyphenylenes, polyphenyls, polyphosphazenes, polypyrroles, polypyrrones, polyquinolines, polyquinoxalines, plysilanes, polysilazanes, polysiloxanes, polysilsesquioxanes, polysulfides, polysulfonamides, polysulfones, polythiazoles, polythioalkylenes, polythioarylenes, polythioethers, polythiomethylenes, polythiophenylenes, polyureas, polyurethanes, polyvinyl acetals, polyvinyl butyrals, and polyvinyl formals. One skilled in the art will further appreciate that the selection of the specific type of polymer will affect the composition and permeability characteristics of the subject microcapsules.

Buffers

Buffers have a vast significance in all areas of science. A buffered solution resists changes in pH when acids or bases are added or when dilution occurs. A buffer is a mixture of an acid and its conjugate base. There must be comparable amounts of the conjugate acid and base, within a factor of 10, to exert significant buffering. Buffers allow for the proper functioning of any biological system and its subcellular components such as proteins and peptide-based molecules. Nearly all biological systems depend on pH. For example, a buffer solution maintains the correct pH for enzymes in many organisms to work. Typically, enzymes function only under very precise conditions. If the pH moves outside of a narrow range, the enzymes slow or stop functioning and can denature. pH directly affects the rate of enzyme-catalyzed reactions.

In some cases, the buffering of a therapeutic agent solution is required and in other cases the buffering of a therapeutic agent solution is preferred to enhance shelf life and stability of a product. In some cases, the buffering of a therapeutic agent solution is preferred to gain a more substantive effect of the agent. The rate of therapeutic agent release is a critical factor in patient care. This invention provides methods and compositions targeted at the microencapsulation of a buffered therapeutic solution capable, for example, of a sustained, prolonged release of the therapeutic agent, a burst release of the therapeutic agent, or a selective variable rate of release of the therapeutic agent (e.g., a quick burst followed by sustained release, or sustained release followed by a quick burst).

Many classes of buffer solutions can be used in the invention, and the choice of buffer depends on the specific pH desired. Examples include, but are not limited to, the following: Phosphate buffered saline which is a solution containing sodium chloride, sodium phosphate, and, in some formulations, potassium chloride and potassium phosphate; 3-([tris(hydroxymethyl)methyl]amino) propane-sulfonic acid (TAPS); N,N-bis(2-hydroxyethyl)glycine (Bicine); tris (hydroxyl-methyl)methylamine (Tris); N-tris(hydroxymethyl)methylglycine (Tricine); 3-[N-Tris-(hydroxymethyl) methylamino]-2-hydroxypropanesulfonic acid (TAPSO); 4-2-hydroxy-ethyl-1-piperazineethanesulfonic acid (HEPES); 2-([tris(hydroxymethyl)methyl]amino)ethanesulfonic acid (TES); 3-(N-morpholino)propanesulfonic acid (MOPS); piperazine-N,N'-bis(2-ethanesulfonic acid) (PIPES); dimethylarsinic acid (Cacodylate); saline sodium citrate (SSC); 2-(N-morpholino)ethanesulfonic acid (MES); Phosphoric acid; citric acid; piperazine-N,N'-bis(3-propane-sulfonic acid (PIPPS); piperazine-N,N'-bis(3-butanesulfonic acid) (PIPBS); N,N'-Diethylethylenediamine-N,N'-bis(3-propanesulfonic acid) (DESPEN); N,N'-diethylpiperazine dihydrochloride (DEPP.2HCl); N,N,N',N'-tetraethyl-ethylenediamine dihydrochloride (TEEN.2HCl); N-2-Acetamidoiminodiacetic acid (ADA); 1,3-Bis[tris(hydroxymethyl) methylamino]propane hydrochloride (BIS-TRIS propane.HCl); N-2-acetamido-2-aminoethanesulfonic acid (ACES); 3-(N-Morpholino)-2-hydroxypropanesulfonic acid (MOPSO); imidazole hydrochloride; 3-(N-morpholino)butanesulfonic acid (MOBS); 4-2-hydroxyethyl-1-piperazinepropane-sulfonic acid (HEPPS); N-tris(hydroxymethyl) methylglycine (TRICINE); glycine amide hydrochloride; Tris(hydroxymethyl)aminomethane hydrochloride (TRIS hydrochloride); glycylglycine; Boric acid; cyclohexylaminoethanesulfonic acid (CHES); 3-(Cyclohexylamino)propane sulfonic acid (CAPS); N,N,N',N'-tetraethylmethylene-diamine dihydrochloride (TEMN.2HCl); HCl and sodium citrate; citric acid and sodium citrate; acetic acid and sodium acetate; $K_2HPO_4$ and $KH_2PO_4$; $Na_2HPO_4$ and $NaH_2PO_4$; N-cyclohexyl-2-aminoethanesulfonic acid; sodium borate; and sodium hydroxide.

It will be known to those skilled in the art that the buffer pH depends on ionic strength and temperature. Compositions can be adjusted accordingly during the synthesis, storage and use of the microencapsulated buffer solution.

Surfactant-Free Inverse Emulsion Polymerization

In a preferred embodiment of surfactant-free inverse emulsion polymerization, a very low molecular weight polyurethane is premixed into the continuous oil phase. Preferably, the molecular weight of the polyurethane is 1,500 to 20,000 g/mole, and more preferably from 1,500 to 8,000 g/mole. Due to the amphiphilic nature of the low molecular weight polyurethane, the polyurethane spends the majority of the time at the interface of the dispersed and continuous phases.

In this embodiment, diol is added to the system to increase the molecular weight of an isocyanate functionalized polyurethane shell. A preferred diol is ethylene glycol. The diol ultimately leads to ethylene oxide linker units in the microcapsule chemical structure. It has been shown in industrial applications that ethylene oxide does not inhibit the flow of ions between electrodes. This approach is useful for understanding the structure-property relationship of the urethane on microcapsule permeability due to the ease with which the chemical structure can be varied in the synthesis of the microcapsules by simply changing the identity of the diol used in the polyurethane wall. In this embodiment, the ion permeability of the microcapsule shell is based on the chemical composition of the diols that act as spacer monomers. The following scheme represents the reaction used to synthesize the microcapsule shell of this embodiment.

block of a polyester added to it to enhance biodegradation. Polylactic acid or polylactide could be incorporated into the microcapsule chemical structure to control biodegradation of the microcapsule.

A second characteristic influencing the permeability of the microcapsule membrane is the shell or wall thickness, which may be varied by varying the ratio of the mass of material used to synthesize the shell to the volume of the dispersed buffered therapeutic agent solution. At a constant stir rate, adding more material relative to the buffered aqueous therapeutic agent phase will lead to formation of thicker microcapsule walls. In a preferred embodiment, the invention comprises a ratio of 1 gram of polyurethane to from 15 to 40 mL of aqueous buffer solution.

Embodiments of the materials of the invention can be formulated such that only one type of buffered therapeutic agent is contained within the core of the microcapsule, or alternatively, a plurality of different types of buffered therapeutic agents, and can be incorporated into one microcapsule.

In other embodiments, a plurality of microcapsules containing one type of buffered additive can be combined in a product with microcapsules containing other additives.

Loading of Microcapsules

The microcapsules of the invention contain semi-permeable polymer shells wherein the permeability functions to release a therapeutic agent both out of the microcapsules and into the microcapsules from the surrounding environment as a result of concentration gradients. Thus, embodiments are contemplated where already formed microcapsules having

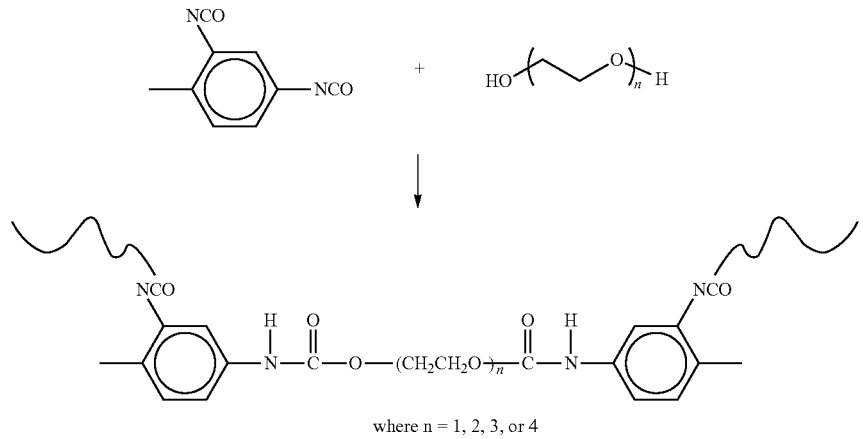

where n = 1, 2, 3, or 4

The length of the ethylene oxide spacer in the microcapsule wall may be varied in order to control ion permeability of the membrane shell. Preferred embodiments include microcapsules using ethylene glycol (n=1) and from 1,4-butanediol (n=2). Preferred embodiments include microcapsules from diols where n=3 (1,6-hexanediol) or 4 (1,8-octanediol). Preferred embodiments include microcapsules from polymeric diols such as polyethylene glycol (also known as polyethylene oxide or polyoxyethylene). Preferred embodiments include polyol monomers capable of forming a crosslinked polymer microcapsule wall. Many classes of polyols can be used in the scope of the invention and the choice depends on the specific desired properties. Examples include, but are not limited to, pentaerythritol and glycerol.

In one embodiment, the microcapsule is biodegradable. The polyurethane prepolymer could, for example, have a none or less than the maximum possible amount of the therapeutic agent dissolved in the buffered solutions in the core can be charged with additional therapeutic agent solution, herein referred to as "loading." Loading also includes "recharging" of microcapsules with buffered solution without therapeutic agents in the presence of the target buffered therapeutic agent and appropriate concentration gradients. The new therapeutic agent can be introduced into the core of partially loaded microcapsules or reintroduced into the core of empty microcapsules by immersing the microcapsules into buffered solutions of highly charged therapeutic agents where the concentration of the therapeutic agent in the buffered solution is higher than the concentration of the therapeutic agent in the buffer solution within the core of the microcapsules. The recharge rate of the microcapsules can depend on but is not limited to the following variables including the concentration gradients of the therapeutic agents, the temperature and the release profile of the particular polymers of the product.

The method of loading a therapeutic agent into a microcapsule that contains only buffer solution is preferred when any heat above normal body temperature is needed in the formation of the microcapsule. This method avoids the use of heat that could cause a peptide-based therapeutic agent to denature.

Therapeutic Agents

As used herein, the term "therapeutic agent" means an agent (e.g., an atom, an ion, a salt, a molecule (such as an inorganic molecule, an organic molecule or a biomolecule (e.g., a peptide, a peptide analog or a protein)), a solid or a liquid) that brings about a beneficial effect to a mammal or any tissue or other subpart thereof.

Many classes of therapeutic agents can be used in the invention. Indeed, these therapeutic agents are envisioned for use in treating a wide array of conditions, such as demineralization of bone; weakness of bone, skin, hair and nails; drying, staining and cracking of skin; tooth sensitivity and discoloration; skin dehydration; and infections of all types. Examples of therapeutic agents include, but are not limited to, the various agents set forth below.

Antimicrobial Agents

Antimicrobial agents are substances that kill or inhibit the growth of microorganisms such as bacteria, fungi or protozoa. Antimicrobial agents can be in the form of a drug that is either microbiocidal or microbiostatic. Antimicrobial agents can be used outside the human body or on non-living objects. Antimicrobial agents that are drugs can come from either natural sources or can be synthetically prepared.

Antimicrobial agents can be used in many different products, such as medical devices, wound dressings, fabrics, and numerous consumer products, both to protect the product from antimicrobial growth or for public health purposes. Natural or synthetic antimicrobial materials have the potential to be included into other materials or used directly on product surfaces or contained within a surface coating.

Natural antimicrobial agents include, but are not limited to, beta lactam antiobiotics such as penicillins or cephalosporins, protein synthesis inhibitors such as aminoglycosides, macrolides, ketolides, tetracyclines, chloramphenicol, and polypeptides. Penicillins include, but are not limited to, penicillin G, procaine penicillin, benzathine penicillin, and penicillin V. Cephalosporins include, but are not limited to, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan and cefoxitin. Aminoglycosides include, but are not limited to, amikacin, arbekacin, gentamicin, kanamycin, neomycin, netilmicin, paromomycin, rhodostreptomycin, streptomycin, tobramycin, and apramycin. Macrolides include, but are not limited to, azithromycin, clarithromycin, dirithromycin, erythromycin, roxithromycin, and telithromycin. Ketolides include, but are not limited to, telithromycin, cethromycin, solithromycin, spiramycin, ansamycin, oleandomycin, carbomycin and tylosin. Naturally occurring tetracyclines include, but are not limited to, tetracycline, chlortetracycline, oxytetracycline, and demeclocycline. Semi-synthetic tetracyclines include, but are not limited to, doxycycline, lymecycline, meclocycline, methacycline, minocycline and rolitetracycline. Polypeptides include, but are not limited to, actinomycin, bacitracin, colistin, and polymyxin B. Synthetic antimicrobial agents include, but are not limited to, sulphonamides, cotrimoxazole, quinolones, antivirals, antifungals, anticancer drugs, antimalarials, antituberculosis drugs, antileprotics and antiprotozoals. Sulphonamide antibacterials may include, but are not limited to, sulfamethoxazole, sulfisomidine, sulfacetamide, sulfadoxine, dichlorphenamide, and dorzolamide. Sulphonamide diuretics include, but are not limited to, acetazolamide, bumetanide, chlorthalidone, clopamide, furosemide, hydrochlorothiazide, indapamide, mefruside, metolazone, and xipamide. Sulphonamide anticonvulsants include, but are not limited to, acetazolamide, ethoxzolamide, sultiame and zonisamide. Other sulfonamide therapeutic agents include, without limitation, celecoxib, darunavir, probenecid, sulfasalazine, and sumatriptan.

Antifungal Agents

Common fungal infections include athlete's foot, ringworm, and candidiasis. Fungi can also cause systemic infections like cryptococcal meningitis. Antifungals work by exploiting differences between mammalian and fungal cells to kill off the fungal organism without dangerous effects on the host. Unlike bacteria, both fungi and humans are eukaryotes.

Antifungal agents can be of the polyene type which includes, but is not limited to, amphotericin B, candicidin, filipin, hamycin, natamycin, nystatin and rimocidin. Antifungal agents can be of the imidazole, triazole, and thiazole types which include, but are not limited to, bifonazole, butoconazole, clotrimazole, econazole, fenticonazole, isoconazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole and abafungin.

Antifungal agents can also be echinocandins which can include, but are not limited to, anidulafungin, caspofungin and micafungin.

Antibacterial Agents

Host defense proteins and peptide-based antibiotic drugs can selectively target and puncture the bacterial cell membrane. Host defense proteins which are part of the innate immune system in the body represent a first line of defense against bacterial attack and primarily exist in the respiratory tract, urogenital tract, gastrointestinal track and epidermal tissues under the skin, all entry points for microbial pathogens in the body. These proteins kill bacteria by targeting bacterial membranes thereby generating an instability of the cellular contents and membrane, which results in the death of the bacteria. Examples include the treatment of bacterial skin infections caused by *Staphylococcus aureus*, or the treatment of other blood stream infections, lung infections and oral mucositis.

An approach to limiting the proliferation of microflora in the oral environment is through topical or systematic application of broad-spectrum antibacterial compounds. The reduction of the number of oral microflora in the mouth results in a direct reduction or elimination of plaque and pocket accumulation together with their damaging acidic metabolite production. The major drawback of this particular approach is that a wide variety of benign or beneficial strains of bacteria are found in the oral environment which may be killed by the same antibacterial compounds in the same manner as the harmful strains. In addition, treatment with antibacterial compounds may select for certain bacterial and fungi, which may then become resistant to the antibacterial compound administered and thus proliferate, unrestrained by the symbiotic forces of a properly balanced microflora population. Thus, the application or administration of broad-spectrum antibiotics alone is ill-advised for the treatment of caries and a more specific, targeted approach is desired.

The appearance of strains of drug-resistant bacteria and the increased number of drug-resistant infections has necessitated new approaches to treat these infections. There are many antibiotics in development for treating resistant bacterial infections. Some of the emerging drugs are peptide-based drugs and peptide analog-drugs. An effective method of delivery in an aqueous solution would be improved by storage in a buffer solution in order to improve shelf life and stability, along with leading to a more substantive effect of the therapeutic agent.

Additional antibacterial agents include, without limitation, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, halogenated carbanilides, halogenated salicylanilides, benzoic esters, halogenated diphenyl ethers, and mixtures thereof. A particularly suitable non-ionic antibacterial agent is a diphenyl ether such as 2,4,4'-trichloro-2'-hydroxydiphenyl ether (Triclosan) and 2,2'-dihydroxy-5,5'-dibromodiphenyl ether. Antifungal agents can be of the allylamines type which includes, but is not limited to, amorolfin, butenafine, naftifine and terbinafine.

Antiviral Agents

Antivirals are used for specific viruses and are typically harmless to the host. Many available drugs available are created to treat infections by retroviruses such as HIV. Important antiretroviral drugs include the class of protease inhibitors. Herpes viruses, best known for causing cold sores and genital herpes, are usually treated with the nucleoside analogue acyclovir. Viral hepatitis is caused by five unrelated hepatotropic viruses and is also commonly treated with antiviral drugs depending on the type of infection. Influenza A and B viruses are important targets for the development new influenza treatments to overcome the resistance to existing neuraminidase inhibitors such as oseltamivir.

Antiparasitic Agents

Antiparasitics are a class of medications which are indicated for the treatment of infection by parasites, such as nematodes, cestodes, trematodes, infectious protozoa, and amoebae.

Antimicrobial Coatings

A surface can be made antimicrobial by providing a coating containing an antibacterial agent that inhibits or diminishes the ability of a microorganism to grow on the surface of a material. Surface contamination has become recognized as a health risk in various settings including clinical, industrial and home. Antimicrobial coatings have been commonly used in the healthcare industry for sterilizing medical devices to prevent hospital-associated infections. Medical devices, surgical instruments, tubing, suture, tape, bandaging, linens and clothing provide a potential environment for many bacteria, fungi, and viruses to grow when in contact with the human body which allows for the transmission of infectious disease. Likewise, implantable devices such as pacemakers and subcutaneous rods provide environments for microbial growth, and would pose less risk of infection if treated with an antimicrobial coating. Antimicrobial surfaces can be functionalized in a variety of different processes. A coating may be applied to a surface that has a chemical compound which is toxic to a microorganism. Other surfaces may be functionalized by attaching a polymer or polypeptide to its surface. In other cases, it is advantageous to have an encapsulated aqueous solution of a peptide-based or peptide analog-based antimicrobial agent embedded in a surface coating.

Anticoagulants and Antithrombotics

Certain medical procedures expose patients to life-threatening blood clots. Patients often receive anticoagulant drugs that reduce or prevent the blood from clotting. Anticoagulant therapy is regularly administered and is a useful aid in the recovery of most patients. However, the use of anticoagulants increases the risk of bleeding, while preserving a sufficient supply of blood. Peptide-based and peptide analog-based drugs have exhibited promise in the maintenance of the antithrombosis/bleeding balance in the patient. This is of value in procedures such as percutaneous coronary intervention and coronary arterial bypass graft.

Anticoagulants include, but are not limited to, coumadins, heparins and its derivatives, low molecular weight heparins, synthetic pentasaccharide inhibitors such as fondaparinux and Idraparinux, direct factor Xa inhibitors, such as rivaroxaban and apixaban and direct thrombin inhibitors including, but not limited to, hirudin, lepirudin, bivalirudin, argatroban and dabigatran.

Anticancer Agents

Therapeutic agents can also be anticancer agents, which include, but are not limited to, alkylating agents such as mechlorethamine, cyclophosphamide, chlorambucil, and ifosfamide. Anticancer agents can be anti-metabolitesor plant alkaloids or terpenoids which include, but are not limited to, vincristine, vinblastine, vinorelbine and vindesine. Anticancer agents can include podophyllotoxin or taxanes. Anticancer agents can be topoisomerase inhibitors including, but not limited to, the camptothecins irinotecan and topotecan, amsacrine, etoposide, etoposide phosphate, and teniposide. Anticancer agents can be cytotoxic antibiotics that include, but are not limited to, actinomycin, anthracyclines, doxorubicin, daunorubicin, valrubicin, idarubicin, epirubicin, bleomycin, plicamycin, and mitomycin. Antiprotozoals can include, but are not limited to, eflornithine, furazolidone, melarsoprol, metronidazole, ornidazole, paromomycin sulfate, pentamidine, pyrimethamine and tinidazole.

Anti-Inflammatory Agents

Anti-inflammatory agents include, but are not limited to, flucinolone and hydrocortisone, ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone.

Antiplaque Agents

Antiplaque (e.g., plaque disrupting) agents can be a form of therapeutic agent. Suitable antiplaque agents include, without limitation, glucoamylase and glucose oxidase.

Desensitizing Agents

Desensitizing, or tooth sensitivity-protecting agents, can be therapeutic agents. Desensitizing agents include, without limitation, potassium salts such as potassium citrate, potassium tartrate, potassium chloride, potassium sulfate and potassium nitrate or sodium nitrate.

Systemic Analgesics

Systemic analgesics include, but are not limited to, aspirin, codeine, acetaminophen, sodium salicylate and triethanolamine salicylate.

Drub Delivery and Indications
  Subcutaneous Drug Delivery
  Biodegradable polymeric systems represent a promising method for delivering many therapeutic agents, including, for example, peptides and peptide analogs. Some polymers undergo a sol-gel transition once administered. A gel can form in situ in response to one or a combination of stimuli including UV-irradiation, pH change, temperature change, and solvent exchange. Some polymeric systems have several advantages over conventional methods, including ease of manufacturing, ease of administration, and biodegradability. There have been challenges, however, to control the release profiles of the incorporated therapeutic agents. It would be advantageous to be able to store a peptide-based or peptide analog-based drug in a microencapsulated buffer solution, wherein the semi-permeable microcapsule could control the rate of release of the therapeutic agent. The microcapsule can be made to biodegrade along with the polymer system in which it is embedded.
  Controlled Release
  The microcapsules and products of the invention can be designed to have different time release profiles, in such a way as to permit controlled time release, also known as sustained release or long-term release, of the therapeutic agents or constituents to effectuate various desired results. Thus, various additives or components of the invention can be released at varying periods of time from each microcapsule. A plurality of microcapsules that contain different concentrations can achieve, in effect, a targeted therapeutic agent release profile.
  Furthermore, the ratios of release times in different types of microcapsules can be incorporated into the design of a single product to optimize the permeability and concentration of the specific biologically active additives or constituents of each type of microcapsule in the product relative to one another and relative to the environment where they are required. Such design enables a product that can deliver a number of buffered therapeutic agents over a controlled time to a particular targeted site without the need for numerous administrations of a product to a patient, thereby minimizing the treatment regimen of the patient.
  For example, a dental product can provide an antibacterial treatment to a targeted tooth surface in the oral cavity. For example, fillings, sealants and cements can be designed to contain the controlled release microcapsules of the invention and to release buffered antimicrobial agents over time to the area of contact with the tooth or tooth material. Sustained release dosage forms of dental products avoid the necessity of frequently administering an active while at the same time achieving a desired level of anti-caries activity in the oral cavity.
  One method for controlling release is selecting a shell polymer having desired permeability. Another method to control permeability and release profile is to control the thickness of the shell layer during synthesis of the microcapsules as described herein.
  The concentration of agents within the microcapsule can also be varied to effect permeability. In a preferred embodiment, buffered therapeutic agents and combinations thereof are incorporated in the microcapsules. Each microcapsule is synthesized with a buffered aqueous solution of a therapeutic agent with a specific targeted range of concentrations.
  For example, tablets comprising the microcapsules of the invention can be produced, wherein the therapeutic agent is not all immediately absorbed, but instead is released gradually and continuously over a period of time from administration. For prolonged shelf life and substantive effects, the therapeutic agent is preferentially stored in a buffered solution.
  In the oral cavity, an instant release or "burst" release of the microcapsules can result upon mechanical agitation of the teeth, such as by use of toothbrushes or dental floss in the oral cavity; by regular chewing, grinding, gritting, clenching or clamping of the teeth or gums; by tongue motion or pressure of the tongue; or by swishing or gargling of liquids by the jaw muscles and motion of other muscles within the internal orifices of the mouth. Both semi-permeable microcapsules and the impermeable microcapsules of the invention, as described above, can be incorporated into products designed for burst release effect.
  Pharmaceutical Compositions
  The compositions of this invention can be in the form of pharmaceutical composition comprising the therapeutic agent-containing microcapsules and a pharmaceutically acceptable carrier. Pharmaceutically acceptable carriers are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Preservatives and other additives may also be present, such as, for example, antimicrobials, antioxidants, chelating agents, inert gases, and the like.
  Bone Restorative Materials
  The compositions of the invention are useful in a variety of bone restorative or regeneration products. There is a need for new materials that can stimulate the body's own regenerative mechanisms and heal tissues. Porous templates that act as scaffolds are thought to be required for three-dimensional bone tissue growth. Bone growth factors have high potential to stimulate bone-forming cells to produce new bone, they are degradable in the body and they bond to bone. Bone restorative or regeneration products may include bone growth factors that could be stored longer or have more substantive effects if stored in a buffered environment within the microcapsule.
  Specific dental products comprising the microcapsules of the invention include dental gels, pastes, rinses, dentifrices, whitening products, breath fresheners, artificial saliva systems, varnishes, desensitizers and other dental products well known in the dental art. Dental restorative materials include, but are not limited to, composite and other solid phase filling materials, adhesives and cements, temporary restorative materials, coatings on implants for the induction of bone growth. Various embodiments of the invention include over-the-counter applications such as toothpastes, bleaching agents, varnishes, sealants, sealers, resin restorative materials, glass ionomers (including resin modified glass ionomers), bioactive glass, compomer restorative materials, giomer restorative materials, oral rinses, any topical preventive or remineralizing agents (liquids, gel mousses, pastes), any rinse including antimicrobial agents, professionally applied and over-the-counter "paint-on" liquids gels, varnishes, sealers, indirect laboratory materials including laboratory resins, denture teeth, denture base materials, dental cements, root canal fillers and sealers, materials used for bone grafting, bone cements, dental implant tissue growth materials, endodontic root filling materials (i.e. apicoectomy materials sometimes called retro-fill materials), pulp capping materials, temporary restorative filling materials, prophy paste, periodontal scaling gels, air abrasion powders for prophylaxis, orthodontic cements, oral surgery extraction socket dressing, cadaver bone, and other bone substitutes.

Embodiments of dental products also include products that can dissolve in the oral cavity upon contact with saliva as a result of enzymatic activity in the oral cavity, such as dissolvable whitening strips. Other products incorporating the microcapsules that have a targeted effect on teeth include chewing gums, candies, lozenges, capsules, tablets and various food items.

In an embodiment where the microencapsulated dental compositions of the specific buffered solutions of antimicrobial agents of the invention allow incorporation of antimicrobial agents into a matrix of polymerizable composites and other solid filling dental restorative materials such as glass ionomer cements, the incorporation of the microencapsulated antimicrobial agents provides a source of bioactive filling materials and adhesives. The use of semi-permeable microcapsules allows the material to release these antimicrobial agents at the interface between the tooth structure and the restorative filling material or adhesive. This interface is particularly vulnerable to bacterial ingress, attack and subsequent secondary caries development. The presence of fluid within this interface can signal possible micro-leakage at the restorative interface but also allow activation of the material to release the antimicrobial agents. Embodiments of the microcapsules of the invention can be designed to release the antimicrobial agents when under mechanical stress at the opening of a space at the tooth/filling interface.

Dental composition embodiments of the invention also comprise a solid phase, such as composites, which offer multiple advantages. Presently, it is unknown to add antimicrobial agents into a resin composite and provide activity of the antimicrobial agents because the antimicrobial agents are likely incorporated or entombed within the resin or plastic insoluble matrix.

Delivery and Indications for Subcutaneous and Topical Therapeutic Agents

Related Therapeutic Products for Topical Use on Hair, Nails, Skin and Other

Epithelial Tissue

There are numerous therapeutic agents that can be delivered to a subject via products such as moisturizers, creams, lotions, foams and gels. Such agents include the following non-limiting examples: antibacterials such as Bactroban or Cleocin; Anthralin (Drithocreme, Micanol and others) for psoriasis; antifungal agents such as Lamisil, Lotrimin and Nizoral for skin conditions such as ringworm and athlete's foot; benzoyl peroxide creams for treating acne; coal tar for treating conditions such as seborrheic dermatitis (usually via shampoos) or psoriasis; corticosteroids for treating skin conditions including eczema via foams, lotions, ointments and creams; retinoids (such as Retin-A and Tazorac) are gels or creams for treating acne; salicylic acid in lotions, gels, soaps, shampoos, and patches, is used to treat acne and warts; antiviral agents such as Valtrex, acyclovir, and Famvir are useful for treating herpes; corticosteroids such as prednisone, and immunosuppressants, such as azathioprine and methotrexate, are useful in treating inflammatory diseases such as eczema and psoriasis; and biologics such as Enbrel, Humira, Remicade, Stelara and Amevive are useful for treating psoriasis as well.

Shampoo

A shampoo is made by combining a surfactant (typically sodium lauryl sulfate and/or sodium laureth sulfate) with a co-surfactant (usually cocamidopropyl betaine) in water to form a thick, viscous liquid. Other shampoo components include salt (e.g., sodium chloride), preservatives and fragrances. Further components are usually added to achieve the following properties: pleasing foam; easy rinsing; minimal skin and eye irritation; thick and creamy feel; good fragrance; low toxicity; biodegradability; and proper pH.

The following are common shampoo ingredients: glycol distearate; silicone; ammonium chloride; ammonium lauryl sulfate; glycol; sodium lauroamphoacetate (cleanser and counter-irritant); polysorbate 20 (abbreviated as PEG(20), penetrant); polysorbate 80 (abbreviated as PEG(80), emulsifier); PEG-150 distearate (thickener); citric acid (antioxidant, pH adjuster and preservative); quaternium-15 (preservative); polyquaternium-10 (conditioning agent); Di-PPG-2 myreth-10 adipate (emollient); and methylisothiazolinone (MIT, preservative).

Hair Conditioner

Hair conditioners contain many types of ingredients. The following are examples: moisturizers (e.g., humectants); reconstructors (e.g., hydrolyzed protein); acidifiers; detanglers (e.g., polymers); thermal protectors (e.g., heat-absorbing polymers); glossers (e.g., silicones such as dimethicone or cyclomethicone); oils (i.e., essential fatty acids); surfactants (cationic); lubricants (e.g., fatty alcohols, panthenol, and dimethicone); sequestrants, for better function in hard water; anti-static agents; and preservatives. Conditioners include, for example, the pack conditioners, leave-in conditioners, ordinary conditioners, and hold conditioners.

Hair Gel

Hair gels, which contain cationic polymers, are hairstyling products that are used to stiffen hair into a particular hairstyle.

Moisturizers

Moisturizers increase the skin's hydration (water content) by reducing evaporation. Naturally occurring skin lipids and sterols as well as artificial or natural oils, humectants, emollients, and lubricants, etc., may be part of the composition of commercial skin moisturizers.

Moisturizers for preserving normal skin contain, e.g., lightweight oils, such as cetyl alcohol, or silicone-derived ingredients, such as cyclomethicone. Moisturizers for treating dry skin contain ingredients such as antioxidants, grape seed oil or dimethicone, and petrolatum (for very dry skin). Moisturizers for treating the effects of aging contain, e.g., petrolatum, antioxidants and alpha hydroxy acids.

Nail Polish

Nail polishes typically contain phthalates (e.g., dibutylphthalate (DBP), dimethylphthalate (DMP), diethylphthalate (DEP)), and toluene.

Additives

As used herein, the terms "additive" and "therapeutic agent" are not mutually exclusive. Although many additives have no known therapeutic role, some additives do have known therapeutic benefits.

In some embodiments, where oral application is desired, a sweetener is employed in products that incorporate the microcapsule compositions of the present invention. Sweeteners among those useful herein include, without limitation, orally acceptable natural or artificial, nutritive or non-nutritive sweeteners. Such sweeteners include, without limitation, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptidebased intense sweeteners, cyclamates, dihydrochalcones, and mixtures thereof. One or more sweeteners can be present in a total amount depending strongly on the particular sweetener(s) selected, Products incorporating the compositions of the present invention, where oral application is desired, optionally comprise a flavoring agent. Flavoring agents among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methyl salicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents are ingredients that provide fragrance and/or other sensory effect in the mouth, including cooling or warming effects. Such ingredients include, for example, menthol, menthyl acetate, menthyl lactate, camphor, *eucalyptus* oil, eucalyptol, anethole, eugenol, *cassia*, oxanone, a-irisone, propenyl guaiethol, thymol, linalool, benzaldehyde, cinnamaldehyde, N-ethyl-p-menthan-3-carboxamine, N,2,3trimethyl-2-isopropylbutanamide, 3-1-menthoxypropane-1, 2-diol, cinnamaldehyde glycerol acetal (CGA), methone glycerol acetal (MGA), and mixtures thereof.

In some embodiments of the invention, the therapeutic agent is a "systemic active" which is used to treat or prevent a disorder which, in whole or in part, is not a disorder of the oral cavity. In various embodiments, the active is an "oral care active" used to treat or prevent a disorder or provide a cosmetic benefit within the oral cavity (e.g., to the teeth, gingiva or other hard or soft tissue of the oral cavity). Oral care actives among those useful in the dental compositions herein include anti-caries agents, tartar control agents, periodontal actives, abrasives, breath freshening agents, malodour control agents, tooth desensitizers, salivary stimulants, and combinations thereof. It is understood that while general attributes of each of the above categories of therapeutic agent may differ, there may some common attributes and any given material may serve multiple purposes within two or more of such categories of agents. These therapeutic agents may preferably be stored in a buffered solution to improve shelf life and provide more substantive effects.

Products comprising the compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof. Products comprising an antioxidant may preferably store the composition containing the antioxidant in a buffered solution to improve shelf life and provide more substantive effects.

Products containing compositions of the present invention optionally comprise an orally acceptable zinc ion source useful, for example, as an antimicrobial, anticalculus or breath-freshening agent. One or more such sources can be present. Suitable zinc ion sources include, without limitation, zinc acetate, zinc citrate, zinc gluconate, zinc glycinate, zinc oxide, zinc sulfate, sodium zinc citrate and the like. The products of the invention can optionally comprise a suitable pH-adjusting agent, including, but not limited to, sodium hydroxide, potassium hydroxide, and ammonium, for controlling the stability and shelf life of a dental product.

Products such as food materials incorporating the compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof. Products comprising a nutrient or nutritional supplement may preferably store the composition containing the nutrient or nutritional supplement in a buffered solution to improve shelf life and provide more substantive effects.

In another embodiment of the invention, the products comprising the microcapsules may further include an antibacterial agent for release onto the bone tissue or dental surface. A wide variety of antimicrobial active compounds may be employed. These actives may generally be classified as halogenated hydrocarbons, quaternary ammonium salts and sulfur compounds. Halogenated hydrocarbons include halogenated derivatives of salicylanilides, carbanilides, bisphenols, diphenyl ethers, anilides of thiophene carboxylic acids and chlorhexidines. Quaternary ammonium compounds include alkyl ammonium, pyridinum, and isoquinolinium salts. Sulfur active compounds include thiuram sulfides and dithiocarbamates. Products comprising an antibacterial agent may preferably store the composition containing the antibacterial agent in a buffered solution to improve shelf life and provide more substantive effects.

In various embodiments of the dental products of the present invention, the dental product comprises an adhesive or adhesion-enhancing agent which serves multiple functions, including enhancing adherence of a composition to the surface of the tooth to be remineralized or whitened. The adhesives are optimized for adhering to the teeth, resisting adherence to non-tooth oral surfaces such as the lips, gingival or other mucosal surfaces, and remaining attached to the teeth for an extended time. Optimization of such aspects may be achieved from varying the physical and chemical properties of a single adhesive or combining different adhesives. In certain embodiments of the present invention, the adhesive polymers in the product are those in which a dental particulate can be dispersed and are well known in the art.

The compositions of this invention can also be incorporated into candies, lozenges, chewing gums, tablets, capsules or other products. Incorporation of the microcapsules into the product can be achieved by, for example, stirring into a warm gum base or coating the outer surface of a gum base, illustrative of which may be jelutong, rubber latex, vinylite resins, and similar compounds desirably with conventional plasticizers or softeners, sugar, glucose, sorbitol or other sweeteners. It is also contemplated herein that the microcapsule compositions of the present invention can be incorporated into a variety of food items.

Each of the instant compositions, products and methods is envisioned for human use. It is also understood that although this specification refers specifically to applications in humans, the invention is also useful for veterinary purposes. Thus, in all aspects, the methods and compositions of the invention are useful for domestic animals such as cattle, sheep, horses and poultry; and for companion animals such as cats and dogs; as well as for other animals.

It will be appreciated by persons skilled in the art that the present invention is not limited to the specific embodiments that have been particularly shown and described hereinabove. Rather the scope of the present invention includes combinations of the features described as well as modifications and variations thereof which would occur to a person of skill in the art upon reading the foregoing description and which are not in the prior art.

EXAMPLES

The following examples set forth the compositions and the synthesis methods of the invention. These experiments demonstrate the feasibility of using the surfactant-free interfacial polymerization of a reverse emulsion to successfully encapsulate buffered solutions of therapeutic agents to create effective therapeutic compositions.

Example 1

A microcapsule composition of the invention was prepared containing a buffered solution of a peptide-based anitimicrobial agent. The composition was prepared by performing an interfacial polymerization in a stable inverse emulsion of phosphate buffer saline solution of a peptide-based antimicrobial agent in a methyl benzoate continuous phase. 6 grams of polyglyceryl-3-polyricinoleate (P3P) was used as the emulsifying agent. The emulsifying agent and 4 grams of a polyurethane polymer were mixed together. The aqueous buffer solution of the peptide-based antimicrobial agent (100 mL of 0.1 M) was added to 210 mL of continuous methyl benzoate oil phase under mixing. 0.2 g of ethylene glycol was subsequently added to the inverse emulsion to complete the interfacial polymerization of the polyurethane polymer at the interface of the dispersed buffered aqueous solution of peptide-based antimicrobial agent droplet. The average size of the microcapsule was controlled by the rate of mixing. Using the method of the invention, the following buffered aqueous solutions of an antimicrobial agent were thereby prepared.

Example 2

A microcapsule composition of the invention was prepared containing a buffered solution of a peptide-based anitimicrobial agent. The composition was prepared by performing an interfacial polymerization in a stable inverse emulsion of phosphate buffer saline solution in a methyl benzoate continuous phase. 6 grams of polyglyceryl-3-polyricinoleate (P3P) was used as the emulsifying agent. The emulsifying agent and 4 grams of a polyurethane polymer were mixed together and added to 210 mL of continuous methyl benzoate oil phase under mixing. 0.2 g of ethylene glycol was subsequently added to the inverse emulsion to complete the interfacial polymerization of the polyurethane polymer at the interface of the dispersed buffered aqueous solution of a peptide-based antimicrobial agent. The microcapsules containing buffer solution were stirred in a solution of a buffered peptide-based antimicrobial agent (100 mL of 0.1 M) while being mixed and heated to 37° C. to effectively load the microcapsule with the antimicrobial agent. Using the method of the invention, the following buffered aqueous solutions of an antimicrobial agent were thereby prepared.

Example 3

A composition of the invention for cavity varnish with antimicrobial capabilities was prepared as follows. A standard cavity varnish containing rosin, ethanol and thymol (97 wt %) were combined with 3 wt % of a microcapsule containing a 0.1 M buffered aqueous solution of an antimicrobial agent.

Example 4

A composition for toothpaste with antimicrobial capabilities was prepared comprising a colloidal binding agent, humectants, preservatives, flavoring agents, abrasives, and detergents. 2 wt % of a microcapsule containing a buffered aqueous solution of a peptide-based antimicrobial agent was incorporated. The antimicrobial agents will be released from the encapsulated buffered solution to improve mineralization of the teeth.

Example 5

A composition for a dental resin composite with remineralization and therapeutic capabilities was prepared as follows. A resin mixture (16 wt % total) was first made by combining urethane dimethacrylate resin with triethyleneglycoldimethacrylate (TEGDMA) resin in a 4/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, microcapsules containing a buffered solution of peptide-based antimicrobial agents.

What is claimed is:

1. A product for treating or reducing the likelihood of caries, comprising a microcapsule composition comprised of a first plurality of microcapsules and a second plurality of microcapsules, said first plurality of microcapsules comprising an amphiphilic polyurethane polymer substantially disposed as a semi-permeable shell around a first buffered solution and at least a first therapeutic agent within said buffered solution in said first plurality of microcapsules wherein the therapeutic agent is an anti-caries, and said second plurality of microcapsules comprising an amphiphilic polyurethane polymer substantially disposed as a semi-permeable shell around a second buffered solution comprising a second therapeutic agent within said second buffered solution in said second plurality of microcapsules, wherein each of the first or second therapeutic agents permeate the shell, and wherein the product is suitable for delivery to a mammal, and wherein the microcapsules are prepared by an interfacial polymerization of a reverse emulsion.

2. The product of claim 1, wherein the first buffered solution is selected from at least one of Ca(NO$_3$)2, K$_2$HPO$_4$ and NaF, wherein the shell is permeable to Ca(NO$_3$)2, K$_2$HPO$_4$ and NaF.

3. The product of claim 1, wherein the second therapeutic agent causes tissue mineralization.

4. The product of claim 1, wherein the first subset of microcapsules has a therapeutic agent release profile that differs from the therapeutic agent release profile of the second subset of microcapsules.

5. The product of claim 1, wherein the buffered solution is an aqueous solution.

6. The product of claim 1, wherein the buffered solution is a non-aqueous solution.

7. The product of claim 1, wherein the second therapeutic agent, is selected from the group consisting of an antimicrobial agent, a tooth-whitening agent, an antibiotic, an anticoagulant, a remineralizing agent, an anti-caries agent, a desensitizing agent, and an anti-inflammatory agent.

8. The product of claim 1, wherein the molecular weight of the polymer is from about 1,000 to about 20,000 g/mole.

9. The product of claim 1, wherein the polymer is cross-linked.

10. The product of claim 1, wherein each of a microcapsule of the first or second plurality of microcapsules has a diameter of from about 1 micron to about 3 mm.

11. The product of claim 1 in the form of a paste, a gel, a foam, a rinse, a dentifrice, a tooth whitening product, a breath freshener, an artificial saliva system, a varnish, a desensitizer, a dental restorative, a composite, an adhesive, a cement, a bioactive glass, a glass ionomer, a compomer, a giomer, a resin, a denture tooth, a denture base material, a root canal filler, a sealer, a chewing gum, a dental implant tissue regeneration material, a pulp capping material and a filling restorative.

12. The product of claim 1 further comprising an additive selected from the group consisting of preservatives, antitartar agents, anticalculus agents, antimicrobial agents, flavorings, sweeteners and dyes.

13. The product of claim 1 further comprising a pharmaceutically acceptable carrier.

* * * * *